(12) United States Patent
Ionasec et al.

(10) Patent No.: US 8,532,352 B2
(45) Date of Patent: Sep. 10, 2013

(54) METHOD AND SYSTEM FOR INTRAOPERATIVE GUIDANCE USING PHYSIOLOGICAL IMAGE FUSION

(75) Inventors: Razvan Ioan Ionasec, Princeton, NJ (US); Ingmar Voigt, Erlangen (DE); Bogdan Georgescu, Plainsboro, NJ (US); Yefeng Zheng, Dayton, NJ (US); Jan Boese, Eckental (DE); Klaus Klingenbeck, Aufseβ (DE); Dorin Comaniciu, Princeton Junction, NJ (US)

(73) Assignee: Siemens Aktiengesellschaft, Munich (DE)

( * ) Notice: Subject to any disclaimer, the term of this patent is extended or adjusted under 35 U.S.C. 154(b) by 238 days.

(21) Appl. No.: 13/267,662

(22) Filed: Oct. 6, 2011

(65) Prior Publication Data
US 2012/0087563 A1   Apr. 12, 2012

Related U.S. Application Data

(60) Provisional application No. 61/390,209, filed on Oct. 6, 2010.

(51) Int. Cl.
*G06K 9/00* (2006.01)

(52) U.S. Cl.
USPC ............ 382/128; 382/131; 382/132; 382/154

(58) Field of Classification Search
USPC .................................. 382/128, 131, 132, 154
See application file for complete search history.

(56) References Cited

U.S. PATENT DOCUMENTS

| | | | |
|---|---|---|---|
| 7,327,872 B2 * | 2/2008 | Vaillant et al. | 382/154 |
| 7,916,919 B2 * | 3/2011 | Zheng et al. | 382/131 |
| 8,423,121 B2 * | 4/2013 | Wang et al. | 600/424 |
| 8,428,690 B2 * | 4/2013 | Li et al. | 600/424 |
| 2010/0070249 A1 * | 3/2010 | Ionasec et al. | 703/2 |

* cited by examiner

*Primary Examiner* — Tom Y Lu

(57) ABSTRACT

A method and system for intraoperative guidance in an off-pump mitral valve repair procedure is disclosed. A plurality of patient-specific models of the mitral valve are generated, each from pre-operative image data obtained using a separate imaging modality. The pre-operative image data from the separate imaging modalities are fused into a common coordinate system by registering the plurality of patient-specific models. A model of the mitral valve is estimated in real-time in intraoperative image data using a fused physiological prior resulting from the registering of the plurality of patient-specific models.

24 Claims, 5 Drawing Sheets

100

110

120

METHOD AND SYSTEM FOR INTRAOPERATIVE GUIDANCE USING PHYSIOLOGICAL IMAGE FUSION

This application claims the benefit of U.S. Provisional Application No. 61/390,209, filed Oct. 6, 2010, the disclosure of which is herein incorporated by reference.

BACKGROUND OF THE INVENTION

The present invention relates to intraoperative guidance for cardiac procedures using medical images, and more particularly, to intraoperative guidance in off-pump mitral valve repair using physiological image fusion.

Percutaneous cardiac interventions are accounting for an increasing amount of all cardiac procedures. Non-invasive image analysis is crucial for off-pump, minimal invasive procedures. Various technologies are rapidly emerging for percutaneous mitral valve repair, such as Edge-to-Edge techniques, Annuloplasty, Chordae Replacement, etc.

Fusion and advanced visualization of medical images, which are complementary to current standards in interventional imaging provide the overall perception and feedback to the surgeons. The traditional way of registering image modalities via image-based methods however has limited capabilities, due to the context-free nature of these methods. This leads in most of the cases to alignment results not tolerable in practice. In particular, interventional procedures are largely guided by 2D+time fluoroscopy sequences, providing low contrast images, which may be difficult to interpret. The limited input and image artifacts induced by the employed devices make the catheter navigation rather challenging and increase the potential risks of cardiac intervention procedures.

BRIEF SUMMARY OF THE INVENTION

The present invention provides a method and system for intraoperative guidance in off-pump mitral valve repair using physiological image fusion. In particular, embodiments of the present invention provide a method and system, which intraoperatively fuses a multitude of information relevant to the mitral valve repair procedure. Such information may include images from multiple modalities, physiological models of the mitral valve in relation to the employed percutaneous devices and prostheses, as well as relevant access paths for the catheter. The integration of high-level information including pre- and intra-operative images with device models and patient specific anatomical models will help to reduce risks and improve treatment results by increasing the overall accuracy of the procedure.

In one embodiment of the present invention, a plurality of patient-specific models of the mitral valve are generated, each from pre-operative image data obtained using a separate imaging modality. The pre-operative image data from the separate imaging modalities are fused into a common coordinate system by registering the plurality of patient-specific models. A model of the mitral valve is estimated in real-time in intraoperative image data using a fused physiological prior resulting from the registering of the plurality of patient-specific models.

These and other advantages of the invention will be apparent to those of ordinary skill in the art by reference to the following detailed description and the accompanying drawings.

DETAILED DESCRIPTION

The present invention relates to intraoperative guidance in off-pump mitral valve repair based on medical image data, such as computed tomography (CT), Dyna CT, echocardiography data, fluoroscopic image data, and magnetic resonance imaging (MRI). Embodiments of the present invention are described herein to give a visual understanding of the heart modeling method. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Embodiments of the present invention provide a method and system, which intraoperatively fuses a multitude of information relevant to the mitral valve repair procedure. Such information may include images from multiple modalities, physiological models of the mitral valve in relation to the employed percutaneous devices and prostheses, as well as relevant access paths for the catheter. The integration of high-level information including pre- and intra-operative images with device models and patient specific anatomical models will help to reduce risks and improve treatment results by increasing the overall accuracy of the procedure.

Figure 1:
FIG. 1 illustrates various percutaneous mitral valve repair techniques.
Figure 1:
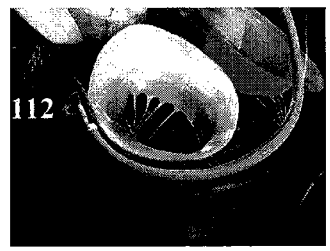
Figure 1:
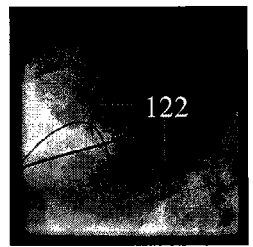

FIG. 1 illustrates various percutaneous mitral valve repair techniques. As illustrated in FIG. 1, image 100 shows "edge-to-edge" mitral valve repair using an Abbott Laboratories MitraClip 102. Image 110 shows an annuloplasty using a Viacor purcutaneous transvenous mitral annuloplasty (PTMA) device 112. Image 120 shows an annuloplasty using an annuloplasty device 122 from Valtech Cardio Ltd.

Figure 2:
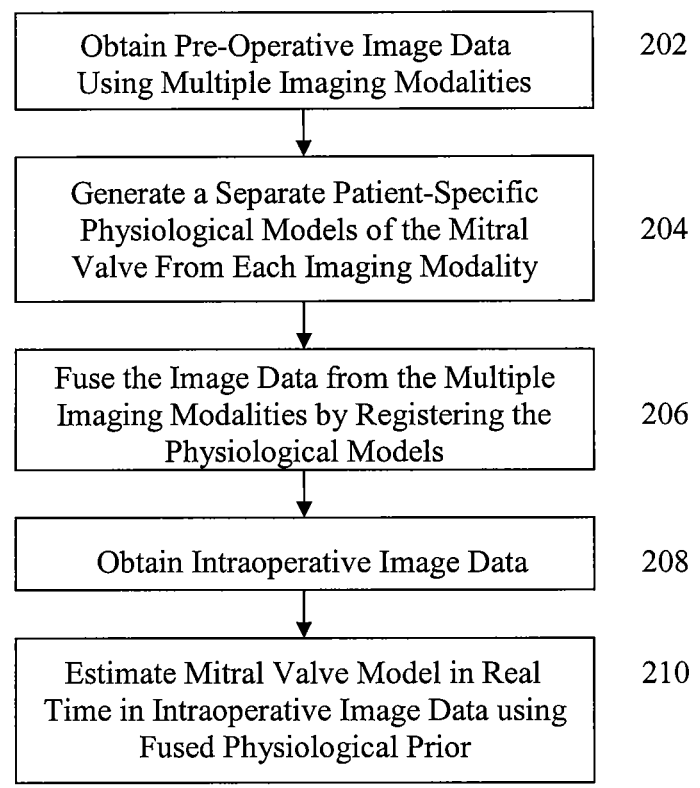
FIG. 2 illustrates a method for intraoperative guidance in a percutaneous mitral valve repair procedure according to an embodiment of the present invention.
Figure 3:
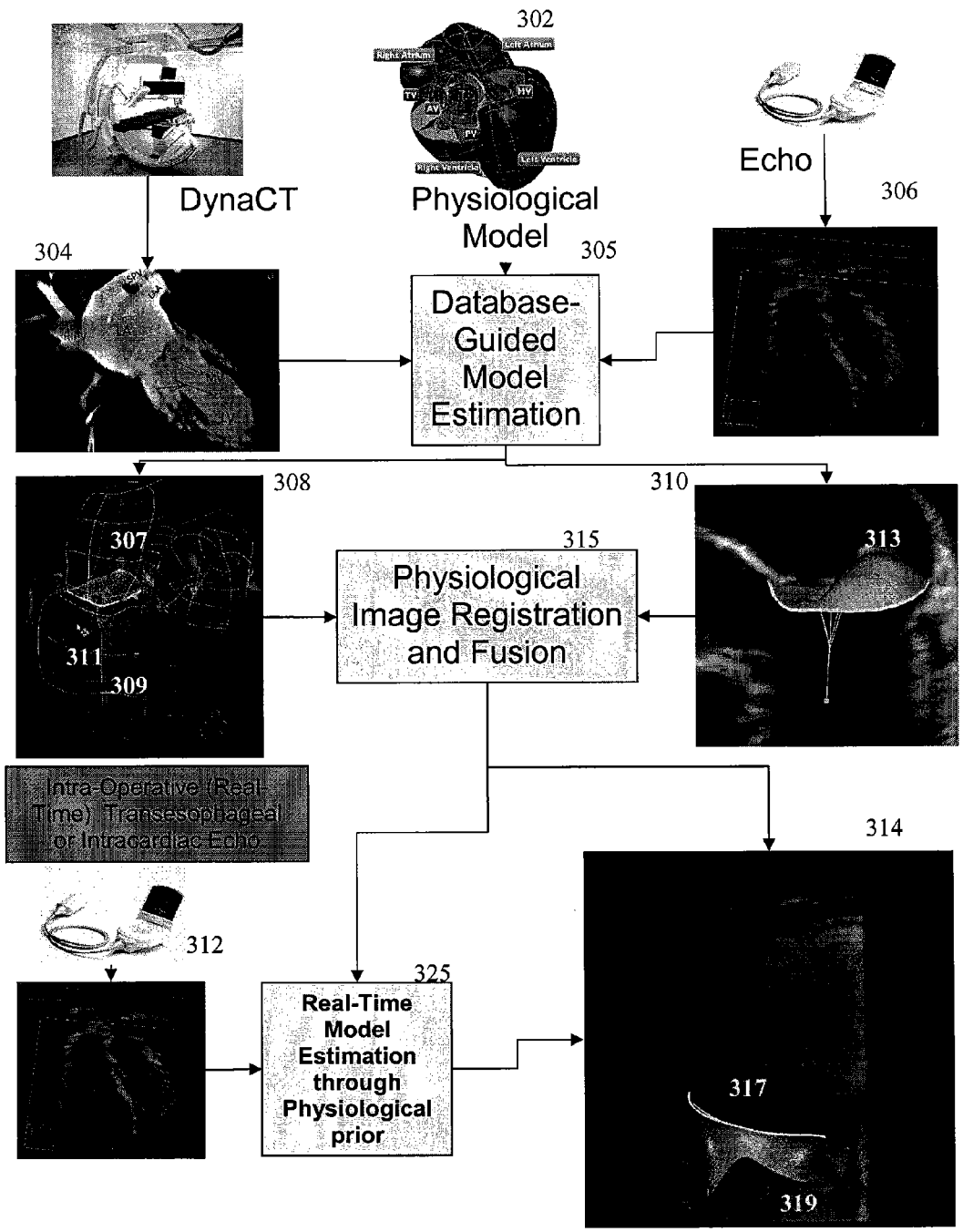
FIG. 3 illustrates an exemplary application of the method of FIG. 2 for intraoperative guidance in an edge-to-edge mitral valve repair procedure according an embodiment of the present invention.

FIG. 2 illustrates a method for intraoperative guidance in a percutaneous mitral valve repair procedure according to an embodiment of the present invention. Although the method is described herein by referencing the example of an edge-to-edge percutaneous mitral valve repair procedure using a MitraClip, the present invention is no limited thereto and may be similarly applied to other percutaneous mitral valve repair procedures. FIG. 3 illustrates an exemplary application of the method of FIG. 2 for intraoperative guidance in an edge-to-edge mitral valve repair procedure according an embodiment of the present invention.

Referring to FIG. 2, at step 202, pre-operative image data is obtained using multiple imaging modalities. For example, image data can be obtained for the same patient using two or more imaging modalities including DynaCT, CT, MR, Ultrasound, PET, SPECT, etc. The image data may be 4D (3D+ time) image data of a cardiac region of a patient. The image data can be obtained directly from an image acquisition device, such as a C-arm image acquisition system, a CT scanner, an MR scanner, and ultrasound device, etc., or may be obtained by loading previously stored image data for a particular patient. In one possible implementation, DynaCT image data can be obtained using a C-arm image acquisition system immediately prior to the mitral valve repair procedure, as a C-arm image acquisition system can capture both the pre-operative 3D DynaCT images and the 3D fluoroscopic images used during the percutaneous mitral valve repair procedure. In the example of FIG. 3 4D DynaCT image data 302 and 4D echocardiography (4D Echo) image data 304 are captured for a patient.

Returning to FIG. 2, at step 204 a separate patient-specific physiological model of the mitral valve is generated from the image data of each imaging modality. Because different imaging modalities capture different details of a patient's anatomy, physiological models generated from different imaging modalities can vary on the particular anatomy included in each model. In one embodiment, the mitral valve annulus and leaflets are modeled preoperatively from four-dimensional (3D+time) echocardiography (4D Echo) image data, while the mitral valve annulus and left atrium are modeled from three-dimensional intraoperative cardiac rotational X-Ray angiography (DynaCT) image data. The patient-specific parameters of the physiological models are estimated from the volumetric images using robust learning-based algorithms as using hierarchical approaches within the Marginal Space Learning (MSL) and/or Trajectory spectrum learning (TSL) frameworks. Detectors can be successively trained using Probabilistic Boosting Trees (PBT) with Haar and Steerable features, and consequently applied to estimate the global location and motion followed by anatomical landmarks and surface structures.

The idea of MSL is not to learn a classifier directly in a full similarity transformation parameter space, but to incrementally learn discriminative classifiers in increasing dimensionality based on annotated training data. As the dimensionality increases, the valid (positive) space region becomes more restricted by previous marginal space classifiers. In order to estimate a physiological model of an anatomic structure, such as a particular heart component, in an image, the estimation of the similarity transformation (i.e., position, orientation, and scale) corresponding to the location of the heart component can be split into three stages: position estimation, position-orientation estimation, and full similarity transformation estimation. A discriminative classifier is trained for each stage based on the training data. All of the discriminative classifiers can be trained as Probabilistic Boosting Trees (PBTs). In addition to reducing the size of the search space, another advantage of MSL is that it is possible to use different features, such as 3D Haar features or steerable features to train the classifier in each marginal space level. Algorithms for generating patient specific-models of the valves and chambers of the heart are described in greater detail in Ionasec, R. et al., "Patient-Specific Modeling and Quantification of the Aortic and Mitral Valves From 4-D Cardiac CT and TEE" *IEEE Transactions on Medical Imaging* 9 (2010), No. 29, pp. 1636-1651; U.S. Pat. No. 7,916,919, issued Mar. 29, 2011, and entitled "System and Method for Segmenting Chambers of a Heart in a Three Dimensional Image"; and United States Published Patent Application No. 2010/0239148, the disclosures of which are each incorporated herein by reference.

As shown in FIG. 3, the DynaCT image data 302, the 4D Echo image data 304, and a mean physiological heart model 306 are all input to the database guided-estimation step 305 (corresponding to step 204 in FIG. 2). The mean physiological heart model 306 is generated based on annotated training data and is fit the image data using database-guide machine learning methods to generate the patient-specific physiological models. The database-guided estimation step 305 generates a first patient-specific physiological model 308 of the chambers and valves of the heart using the DynaCT image data 302 and a second patient-specific physiological model 310 of the mitral valve annulus and leaflets (313) using the 4D echo image data 304. The first physiological model 310 includes the mitral valve annulus 307 and the left ventricle 309.

The preoperative physiological models are used to plan the procedure. For example, in the case of Edge-to-Edge repair the optimal point of septum puncture, i.e., the point of attachment of the MitraClip device, is determined and can then be displayed and targeted throughout the procedure. The optimal point of septum puncture 311 is shown in physiological model 310 of FIG. 3.

Returning to FIG. 2, at step 206, the image data from the various imaging modalities is fused by registering the patient-specific physiological models generated for each imaging modality. In this step, an intra-operative physiological image registration into a common coordinate system is performed. The traditional way of registering image modalities (e.g., CT, MR, Ultrasound, Pet, SPECT) is through image-based methods in which a measure of similarity is defined together with a set of allowed rigid/non-rigid transformations and optimization is involved to maximize the similarity measure subject to the allowed transformations. While the two-dimensional mono-modal problem has been partially solved, efforts for multi-modal registration of higher dimensional images have remained largely academic with few methods adopted in clinical practice. The context-free nature of these methods is one of the main limitations, which leads in most of the cases to alignment results not tolerable in practice.

According to an embodiment of the present invention, the image registration uses correspondence provided by the fitted patient-specific physiological models to establish spatial and temporal alignment of the underlying images. One advantage of this approach is the exploitation of high-level prior knowledge of the underlying physiology, which is implemented using database-guided model estimation techniques that are robust to image alterations due to noise and artifacts but also due to pathology and individual subject characteristics. The model correspondences across time and modalities are obtained using a sampling method in local anatomical coordinates. In order to solve the registration, the parameters of a pre-defined transformation, which maps predetermined pairs of points corresponding to the same locations in different models, are estimated. A possible mapping function and details for estimating this mapping function are described in United States Published Patent Application No. 2010/0067768, the disclosure of which is incorporated herein by reference.

As shown in FIG. 3, the first and second patient-specific physiological models 308 and 310 are input to the physiological image registration and fusion step 315 (corresponding to step 206 of FIG. 2). The physiological image registration and fusion step 315 determines transformation parameters to register the 4D echo data and the DynaCT data to a common coordinate system by registering corresponding points of the first and second patient-specific physiological models 308 and 310. For example, corresponding points of the mitral valve annulus can be used to register the first and second patient-specific physiological models 308 and 310. In one possible implementation, the second patient-specific physiological model 310 is registered to the coordinate system of the first patient-specific physiological model 308. Since the DynaCT images are acquired on the same C-arm device as the fluoroscopic images used in the mitral valve repair procedure, registering the 4D echo data to the coordinate system of the DynaCT images allows for simplified overlay of the 4D echo data on the intraoperative fluoroscopic images. The registration of the first and second patient-specific physiological models 308 and 310 creates a fused physiological prior that can be fit to intraoperative image data to help guide the mitral valve repair procedure.

Returning to FIG. 2, at step 208, intraoperative image data is obtained in the percutaneous mitral valve repair procedure. The intraoperative image data can be a sequence of fluoroscopic images obtained in real time during the procedure. In one implementation, the fluoroscopic images are acquired using an X-ray scanner of a C-arm image acquisition system. Other intraoperative image data may also be acquired in real time during the procedure, such as transesophageal or intracardiac echocardiography (ECG) data, and 4D TEE image data.

At step 210, the fused physiological prior is used to estimate the mitral valve model in the frames of intraoperative image data. In particular, the fused physiological model can be spatially registered with the fluoroscopic images based on the mapping parameters determined in step 206 and can be temporally registered with the fluoroscopic images based on a concurrently recorded electrocardiogram (ECG) signal. The model is then locally adjusted, e.g., using database-guided machine learning based methods, to track the mitral valve in the current fluoroscopic image frame. The estimated mapping and a concurrently recorded electrocardiogram (ECG) signal enables for joint visualization of live Fluoroscopy (2D+time) overlaid with the spatially and temporally co-registered 4D Echo and physiological models as the spatial relationship of the Fluoroscopy sequence and DynaCT images is known via machine coordinates. Real-Time intraoperative tracking and visualization of the employed devices and instruments used in the mitral valve repair procedure from the fluoroscopic overlay is performed, for example using methods described in United States Published Patent Application No. 2010/0121181, the disclosure of which is incorporated herein by reference. Alongside with the visualization of the transvenous, transarterial, transapical or transfemoral access paths for the catheter, this enables for advanced targeting and guidance to the mitral septum puncture point as highlighted in the example of FIG. 3.

In order to provide visual feedback about the deformation of the anatomy introduced by the collision with the instruments and their application, real-time intraoperative tracking and visualization of the mitral valve model from intra operative 4D TEE or/and intracardiac Echocardiogrpahy (ICE) is performed. The pre-operatively obtained physiological model and the temporal alignment/synchronization with the ECG signal significantly reduces the computation time and enables for real-time processing. In order to also enable for real-time tracking of larger deformations, as introduced by the devices and instruments, the database-guided machine learning based computations may be performed on a Graphics Processing Units (GPU) and distributed across multiple computer systems as described in U.S. patent application Ser. No. 13/228,505, filed Sep. 9, 2011, entitled "Method and System for Evaluation Using Probabilistic Boosting Trees", the disclosure of which is incorporated herein by reference.

Figure 4:
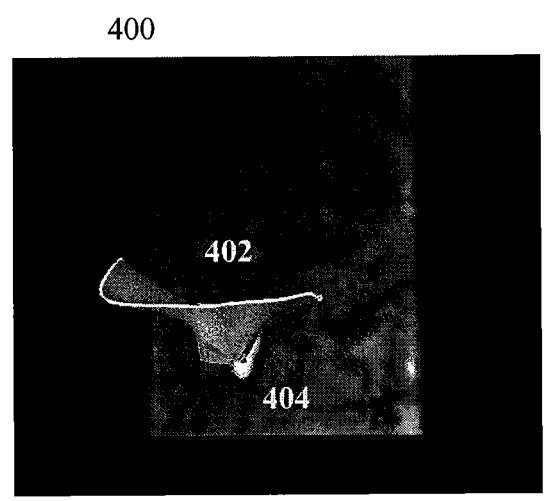
FIG. 4 illustrates a fluoroscopic image frame showing a mitral valve model when a MitraClip is attached to the mitral valve.

As shown in FIG. 3, the real-time model estimation through physiological prior step 325 (corresponding to step 210) converts intraoperative 4D echo image data 312 obtained during the procedure to the same coordinate system as intraoperative fluoroscopic images using the mapping parameters determined in the physiological image registration and fusion step 315. The real-time model estimation through physiological prior step 325 overlays the fused mitral valve model prior onto a fluoroscopic image frame 314. The spatial alignment of the fused mitral valve model prior is determined based on the mapping parameters determined based on the registration of the two patient-specific physiological models 308 and 310 and the temporal alignment is determined by synchronizing the fused mitral valve model prior with a concurrent ECG signal. It can be noted that the patient-specific physiological models are 4D models, such that each is actually a sequence of 3D models over a cardiac cycle. Accordingly, based on the ECG signal the 3D mitral valve model at a point in the cardiac cycle closest to each fluoroscopic image frame can be selected. The mitral valve model prior is then adjusted based on the concurrent 4D echo data to track the mitral valve model in the current frame, and the resulting mitral valve model 317 is overlaid on the fluoroscopic image frame 314. The MitraClip 319 is tracked in the fluoroscopic image to the target mitral septum point determined using the overlaid fused mitral valve model. The devices (e.g., the MitraClip, catheter, etc.) and the mitral valve model are tracked in each frame until the procedure is complete. FIG. 4 illustrates a fluoroscopic image frame 400, showing the tracked mitral valve model 402 when the MitraClip 404 is attached to the mitral valve.

Figure 5:
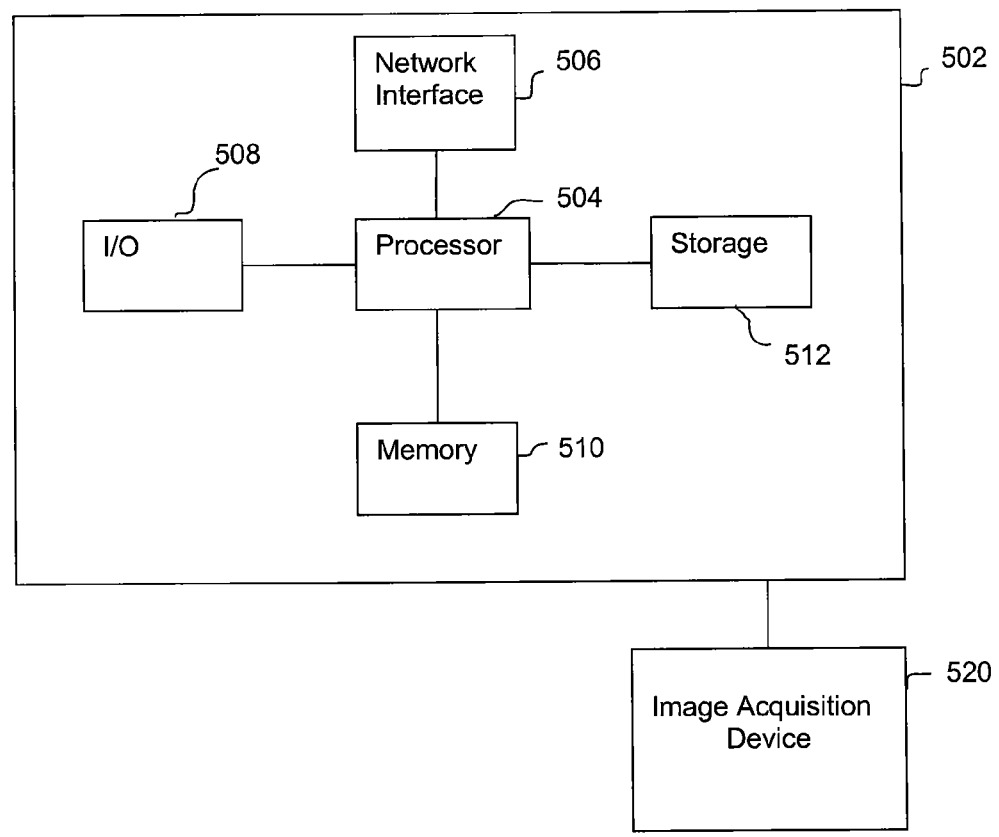
FIG. 5 is a high-level block diagram of a computer capable of implementing the present invention.

The above-described methods for intraoperative guidance in a percutaneous mitral valve repair procedure may be implemented on a computer using well-known computer processors, memory units, storage devices, computer software, and other components. A high-level block diagram of such a computer is illustrated in FIG. 5. Computer 502 contains a processor 504, which controls the overall operation of the computer 502 by executing computer program instructions which define such operation. The computer program instructions may be stored in a storage device 512 (e.g., magnetic disk) and loaded into memory 510 when execution of the computer program instructions is desired. Thus, the steps of the methods of FIGS. 2 and 3 may be defined by the computer program instructions stored in the memory 510 and/or storage 512 and controlled by the processor 504 executing the computer program instructions. An image acquisition device 520, such as a C-arm image acquisition system, ultrasound device, etc., can be connected to the computer 502 to input image data to the computer 502. It is possible to implement the image acquisition device 520 and the computer 502 as one device. It is also possible that the image acquisition device 520 and the computer 502 communicate wirelessly through a network. The computer 502 also includes one or more network interfaces 506 for communicating with other devices via a network. The computer 502 also includes other input/output devices 508 that enable user interaction with the computer 502 (e.g., display, keyboard, mouse, speakers, buttons, etc.). Such input/output devices 508 may be used in conjunction with a set of computer programs as an annotation tool to annotate volumes received from the image acquisition device 520. One skilled in the art will recognize that an implementation of an actual computer could contain other components as well, and that FIG. 5 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for intraoperative guidance in a percutaneous mitral valve procedure comprising:
    generating a plurality of patient-specific models of the mitral valve, each from pre-operative image data obtained using a separate imaging modality;
    fusing the pre-operative image data from separate imaging modalities into a common coordinate system by registering the plurality of patient-specific models; and
    estimating a model of the mitral valve in real-time in intraoperative image data using a fused physiological prior resulting from the registering of the plurality of patient-specific models.

2. The method of claim 1, wherein the step of generating a plurality of patient-specific models of the mitral valve, each from pre-operative image data obtained using a separate imaging modality comprises:
    generating each of the plurality of patient specific models using database-guided machine learning based model estimation.

3. The method of claim 1, wherein the step of generating a plurality of patient-specific models of the mitral valve, each from pre-operative image data obtained using a separate imaging modality comprises:
    generating a first patient-specific physiological model including the mitral valve annulus and leaflets using 4D echocardiography image data; and
    generating a second patient-specific physiological model including the mitral valve annulus and the left ventricle using DynaCT image data.

4. The method of claim 3, wherein the step of fusing the pre-operative image data from separate imaging modalities into a common coordinate system by registering the plurality of patient-specific models comprises:
    determining a set of mapping parameters to register corresponding points in the first and second patient-specific physiological models.

5. The method of claim 4, wherein the step of estimating a model of the mitral valve in real-time in intraoperative image data using a fused physiological prior resulting from the registering of the plurality of patient-specific models comprises:
    registering intraoperative echocardiography image data to intraoperative fluoroscopic image data based on the set of mapping parameters;
    overlaying the fused physiological prior on a current frame of the intraoperative fluoroscopic image data; and
    adjusting the fused physiological prior in the current frame of the intraoperative fluoroscopic image data based on the registered intraoperative echocardiography data.

6. The method of claim 5, wherein the step of overlaying the fused physiological prior on a current frame of the intraoperative fluoroscopic image data comprises:
    temporally registering the fused physiological prior to the current frame of the intraoperative fluoroscopic image data based on an electrocardiogram signal acquired concurrently to the intraoperative fluoroscopic image data.

7. The method of claim 1, further compromising:
    tracking a mitral valve repair device in real-time in the intraoperative image data.

8. The method of claim 7, wherein the step of tracking a mitral valve repair device in real-time in the intraoperative image data comprises:
    tracking the mitral valve repair device in the intraoperative image data to a target point visualized by the model of the mitral valve estimated in the intraoperative image data.

9. An apparatus for intraoperative guidance in a percutaneous mitral valve procedure comprising:
    means for generating a plurality of patient-specific models of the mitral valve, each from pre-operative image data obtained using a separate imaging modality;
    means for fusing the pre-operative image data from separate imaging modalities into a common coordinate system by registering the plurality of patient-specific models; and
    means for estimating a model of the mitral valve in real-time in intraoperative image data using a fused physiological prior resulting from the registering of the plurality of patient-specific models.

10. The apparatus of claim 9, wherein the means for generating a plurality of patient-specific models of the mitral valve, each from pre-operative image data obtained using a separate imaging modality comprises:
    means for generating each of the plurality of patient specific models using database-guided machine learning based model estimation.

11. The apparatus of claim 9, wherein the means for generating a plurality of patient-specific models of the mitral valve, each from pre-operative image data obtained using a separate imaging modality comprises:
    means for generating a first patient-specific physiological model including the mitral valve annulus and leaflets using 4D echocardiography image data; and
    means for generating a second patient-specific physiological model including the mitral valve annulus and the left ventricle using DynaCT image data.

12. The apparatus of claim 11, wherein the means for fusing the pre-operative image data from separate imaging modalities into a common coordinate system by registering the plurality of patient-specific models comprises:
    means for determining a set of mapping parameters to register corresponding points in the first and second patient-specific physiological models.

13. The apparatus of claim 12, wherein the means for estimating a model of the mitral valve in real-time in intraoperative image data using a fused physiological prior resulting from the registering of the plurality of patient-specific models comprises:
    means for registering intraoperative echocardiography image data to intraoperative fluoroscopic image data based on the set of mapping parameters;
    means for overlaying the fused physiological prior on a current frame of the intraoperative fluoroscopic image data; and
    means for adjusting the fused physiological prior in the current frame of the intraoperative fluoroscopic image data based on the registered intraoperative echocardiography data.

14. The apparatus of claim 13, wherein the means for overlaying the fused physiological prior on a current frame of the intraoperative fluoroscopic image data comprises:
    means for temporally registering the fused physiological prior to the current frame of the intraoperative fluoroscopic image data based on an electrocardiogram signal acquired concurrently to the intraoperative fluoroscopic image data.

15. The apparatus of claim 9, further compromising:
means for tracking a mitral valve repair device in real-time in the intraoperative image data.

16. The apparatus of claim 15, wherein the step of tracking a mitral valve repair device in real-time in the intraoperative image data comprises:
means for tracking the mitral valve repair device in the intraoperative image data to a target point visualized by the model of the mitral valve estimated in the intraoperative image data.

17. A non-transitory computer readable medium encoded with computer executable instructions for intraoperative guidance in a percutaneous mitral valve procedure, the computer executable instructions defining steps comprising:
generating a plurality of patient-specific models of the mitral valve, each from pre-operative image data obtained using a separate imaging modality;
fusing the pre-operative image data from separate imaging modalities into a common coordinate system by registering the plurality of patient-specific models; and
estimating a model of the mitral valve in real-time in intraoperative image data using a fused physiological prior resulting from the registering of the plurality of patient-specific models.

18. The non-transitory computer readable medium of claim 17, wherein the computer executable instructions defining the step of generating a plurality of patient-specific models of the mitral valve, each from pre-operative image data obtained using a separate imaging modality comprise computer executable instructions defining the step of:
generating each of the plurality of patient specific models using database-guided machine learning based model estimation.

19. The non-transitory computer readable medium of claim 17, wherein the computer executable instructions defining the step of generating a plurality of patient-specific models of the mitral valve, each from pre-operative image data obtained using a separate imaging modality comprise computer executable instructions defining the steps of:
generating a first patient-specific physiological model including the mitral valve annulus and leaflets using 4D echocardiography image data; and
generating a second patient-specific physiological model including the mitral valve annulus and the left ventricle using DynaCT image data.

20. The non-transitory computer readable medium of claim 19, wherein the computer executable instructions defining the step of fusing the pre-operative image data from separate imaging modalities into a common coordinate system by registering the plurality of patient-specific models comprise computer executable instructions defining the step of:
determining a set of mapping parameters to register corresponding points in the first and second patient-specific physiological models.

21. The non-transitory computer readable medium of claim 20, wherein the computer executable instructions defining the step of estimating a model of the mitral valve in real-time in intraoperative image data using a fused physiological prior resulting from the registering of the plurality of patient-specific models comprise computer executable instructions defining the steps of:
registering intraoperative echocardiography image data to intraoperative fluoroscopic image data based on the set of mapping parameters;
overlaying the fused physiological prior on a current frame of the intraoperative fluoroscopic image data; and
adjusting the fused physiological prior in the current frame of the intraoperative fluoroscopic image data based on the registered intraoperative echocardiography data.

22. The non-transitory computer readable medium of claim 21, wherein the computer executable instructions defining the step of overlaying the fused physiological prior on a current frame of the intraoperative fluoroscopic image data comprise computer executable instructions defining the step of:
temporally registering the fused physiological prior to the current frame of the intraoperative fluoroscopic image data based on an electrocardiogram signal acquired concurrently to the intraoperative fluoroscopic image data.

23. The non-transitory computer readable medium of claim 17, further compromising computer executable instructions defining the step of:
tracking a mitral valve repair device in real-time in the intraoperative image data.

24. The non-transitory computer readable medium of claim 23, wherein the computer executable instructions defining the step of tracking a mitral valve repair device in real-time in the intraoperative image data comprise computer executable instructions defining the step of:
tracking the mitral valve repair device in the intraoperative image data to a target point visualized by the model of the mitral valve estimated in the intraoperative image data.

* * * * *